United States Patent [19]

Lown

[11] Patent Number: 5,338,473

[45] Date of Patent: Aug. 16, 1994

[54] AQUEOUS BETA COBALTOUS HYDROXIDE AND METHOD FOR MAKING

[75] Inventor: Jean A. Lown, St. Paul, Minn.

[73] Assignee: Minnesota Mining and Manufacturing Company, St. Paul, Minn.

[21] Appl. No.: 31,033

[22] Filed: Mar. 11, 1993

Related U.S. Application Data

[60] Continuation of Ser. No. 771,488, Oct. 4, 1991, abandoned, which is a division of Ser. No. 447,668, Dec. 8, 1989, Pat. No. 5,057,299.

[51] Int. Cl.$^5$ .................................................. C09D 5/23
[52] U.S. Cl. ......................... 252/62.51; 252/182.33; 423/139; 423/265; 556/147; 556/148; 556/149
[58] Field of Search ................ 556/147, 148, 149; 423/139, DIG. 14, 265; 252/62.51, 182.33

[56] References Cited

U.S. PATENT DOCUMENTS

| 2,075,230 | 3/1937 | Schatz | 556/147 |
| 2,338,128 | 1/1944 | Minich | 556/147 |
| 2,389,873 | 11/1945 | Schiller | 556/147 |
| 2,950,172 | 8/1960 | Pincott et al. | 423/592 |
| 3,038,899 | 6/1962 | Sifferd | 556/148 |
| 3,193,381 | 7/1965 | George et al. | 423/139 |
| 4,096,090 | 6/1978 | Noack | 252/389.53 |
| 4,224,411 | 9/1980 | Chibata et al. | 435/106 |
| 4,278,610 | 7/1981 | Maurer et al. | 556/149 |

FOREIGN PATENT DOCUMENTS

| 54-75597 | 6/1979 | Japan. | |
| 56-34145 | 4/1981 | Japan. | |
| 61-100606 | 6/1985 | Japan. | |
| 60-263328 | 12/1985 | Japan. | |
| 61-163123 | 7/1986 | Japan. | |
| 63-103830 | 5/1988 | Japan. | |
| 63-134668 | 6/1988 | Japan | 252/62.51 |

OTHER PUBLICATIONS

M. Booy et al., Can. J. Chem., 1977, vol. 55, pp. 1770–1776 no month.
R. S. Sapieszko et al., Corrosion–NACE, 1980, vol. 36, pp. 522–530 no month.
Weiser et al., Journal of Physical Chemistry, vol. 36, pp. 722–734 (1932) no month.
Basavalingu et al., Proc. Int. Symp. Hydrotherm. React., 1st, Meeting date 1982, pp. 738–746 no month.
Masterton et al., Chemical Principles, pp. 54–56 (1977) no month.

Primary Examiner—Gary P. Straub
Assistant Examiner—N. M. Nguyen
Attorney, Agent, or Firm—Gary L. Griswold; Walter N. Kirn; David B. Kagan

[57] ABSTRACT

Beta cobaltous hydroxide is synthesized by decomposing the complex formed between cobaltous ions and a suitable complexing agent under hydrothermal conditions. Cobaltous ion and complexing agent are combined in an aqueous medium, wherein the molar ratio of the cobaltous ion to the complexing agent is about one or more. Hydroxide ion is added, wherein the molar ratio of hydroxide ion to cobaltous ion is more than about 2. The resulting admixture is heated under hydrothermal conditions for precipitating beta cobaltous hydroxide. The method provides improved control over the size and shape of the beta cobaltous hydroxide reaction product. The beta cobaltous hydroxide can be reduced to form magnetic particles of cobalt metal.

3 Claims, No Drawings

AQUEOUS BETA COBALTOUS HYDROXIDE AND METHOD FOR MAKING

This is a continuation of application No. 07/771,488 filed Oct. 4, 1991, now abandoned, which is a division of application No. 07/447,668 filed Dec. 8, 1989, now issued as U.S. Pat. No. 5,057,299.

FIELD OF THE INVENTION

This invention relates to the synthesis of beta cobaltous hydroxide under hydrothermal conditions. This invention also relates to a novel, aqueous admixture suitable for hydrothermal treatment to prepare beta cobaltous hydroxide.

BACKGROUND OF THE INVENTION

The trend in the magnetic recording industry is towards higher density recording. Higher density recording requires materials with improved signal output at shorter wavelengths. Higher density recording also requires materials in which self-demagnetization can be minimized as much as possible.

One material that shows great potential for high density recording applications is cobalt metal. A cobalt metal particle can have a platelet-shape and a close-packed, hexagonal crystallographic structure. Cobalt metal particles with a close-packed, hexagonal, platelet shape have an easy axis of magnetization that is perpendicular to the plane of the particle. Such cobalt metal particles have high saturation magnetization, over 100 emu/g, and coercivities of up to 2000 Oe.

Cobalt metal particles suitable for magnetic recording are obtained by the reduction of pink, hexagonal, platelet-shaped beta cobaltous hydroxide. Various methods for making the beta cobaltous hydroxide precursor are known in the art. In one typical method, beta cobaltous hydroxide is made by reacting a cobaltous salt in an alkaline solution to form a precipitate of beta cobaltous hydroxide. This direct precipitation method is described in each of the Japanese publications JP54-75597, JA60-263328, and JP61-163123.

Unfortunately, the direct precipitation method provides insufficient control for adjusting the average particle size of the beta cobaltous hydroxide reaction product beyond a very limited range. What was needed in the art was a method of making beta cobaltous hydroxide in which a desired average particle size could be easily obtained over a relatively broader size range, while at the same time maintaining uniform particle shape and a narrow particle size distribution.

SUMMARY OF THE INVENTION

The present invention relates to an improved method for making beta cobaltous hydroxide. It has been discovered that beta cobaltous hydroxide can be synthesized by decomposing the complex formed between cobaltous ions and a suitable complexing agent under hydrothermal conditions in basic solution. The present invention provides a significantly improved method of making beta cobaltous hydroxide in which a desired average particle size can be easily obtained over a relatively broad size range, while at the same time maintaining hexagonal, platelet particle shape and a narrow particle size distribution.

The beta cobaltous hydroxide according to the present invention can be reduced to form magnetic particles of cobalt metal. The magnetic particles of cobalt metal thus formed have an electromagnetic performance suitable for magnetic recording applications, such as high density magnetic recording.

One aspect of the present invention concerns a novel composition that is useful for the hydrothermal synthesis of beta cobaltous hydroxide. The composition is an admixture of ingredients comprising a cobaltous ion, a suitable complexing agent, a hydroxide ion, and an aqueous medium.

The cobaltous ion is derived from a cobaltous salt which may contain any of a variety of counter ions. The concentration of cobaltous ion in the admixture is not critical, so long as the concentration of the cobaltous salt is less than its saturation concentration prior to the addition of the hydroxide ion, and so long as the molar ratio of the cobaltous ion to the other ingredients is within the ranges discussed hereinafter. It is desirable, however, that sufficient cobaltous ion is present to provide desired yields.

The complexing agent has at least one functional group, and preferably two functional groups, capable of acting as a Lewis base towards the cobaltous ion. Additionally, the complexing agent is capable of forming a water-soluble complex with the cobaltous ion. It is also believed that the complexing agent stabilizes alpha cobaltous hydroxide in basic solution at about room temperature. The molar ratio of the cobaltous ion to the complexing agent in admixture is about one or more.

The hydroxide ion is derived from a hydroxide base which may contain any of a variety of counter ions. The molar ratio of the hydroxide ion to the cobaltous ion in admixture is at about 2 or more.

The aqueous medium is preferably deionized water having a conductivity of about 50 $\mu$mhos or less.

In another aspect, the present invention concerns a novel, hydrothermal method for making aqueous, platelet-shaped, hexagonal beta cobaltous hydroxide. Hydrothermal conditions means that the reaction takes place in an aqueous reaction medium at an elevated pressure within the specified temperature range. The elevated pressure is not critical as long as the pressure is sufficient to constrain the aqueous reaction medium to the liquid phase. Batch and continuous methods are within the scope of the invention.

The method of the present invention comprises combining a cobaltous ion, a suitable complexing agent, and an aqueous medium to form an aqueous solution. At least about two moles of a hydroxide ion are added to the aqueous solution for each mole of cobaltous ion, thereby forming an admixture of ingredients comprising the cobaltous ion, the complexing agent, the hydroxide ion, and the aqueous medium. After adding the hydroxide ion, the admixture is heated under hydrothermal conditions to a reaction temperature of from about 100° C. to about 268° C. The admixture is maintained under hydrothermal conditions at the reaction temperature for a time sufficient to precipitate the cobaltous ion as beta cobaltous hydroxide.

In the described method, the complexing agent, the molar ratio of the cobaltous ion to the complexing agent, the molar ratio of the hydroxide ion to the cobaltous ion, the aqueous medium, and the concentration of the cobaltous ion in admixture are as defined above.

The present invention provides excellent control over the average particle size of the beta cobaltous hydroxide reaction product. Starting with the same admixture, a desired average particle size ranging from about 0.05 $\mu$m to about 0.5 $\mu$m or more can be easily obtained merely by adjusting the reaction temperature. Further control is achieved by adjusting the concentration of starting materials in the admixture or by adjusting the reaction time.

Practical tests have shown that such control is not provided by the direct precipitation method. Although average particle size generally increases with higher reaction temperature using the direct precipitation method, it has been found that the average particle size varies within a relatively narrow range between the lowest available temperature (0° C.) and the highest available temperature (100° C.). Temperatures outside this range are not available using the direct precipitation method, since water freezes below 0° C. and vaporizes above 100° C.

DESCRIPTION OF THE PREFERRED EMBODIMENTS

As described above, beta cobaltous hydroxide can be synthesized by decomposing the complex formed between the cobaltous ion and a complexing agent under hydrothermal conditions in basic solution. The cobaltous ion is derived from a cobaltous salt which may contain any of a variety of counter ions. Examples of suitable counter ions include, but are not limited to, sulfate, or nitrate. It has been found that varying the counter ion for the cobaltous salt has a minimal effect upon the particle morphology or size of the beta cobaltous hydroxide reaction product.

The concentration of the cobaltous ion in the aqueous solution is not critical so long as this concentration is less than the saturation concentration of the cobaltous salt prior to the addition of the hydroxide ion and so long as the desired relative proportions of ingredients are maintained. If the concentration is too low, however, the yield of beta cobaltous hydroxide may be too low to be efficient or economical for commercial applications. On the other hand, if the concentration is too high, then the solution may be too sensitive to changes in processing parameters, such as temperature, concentrations of individual components, and the like, resulting in undesirable precipitation and fouling of the processing equipment.

Complexing agents useful in the present invention have at least one functional group capable of acting as a Lewis base towards the cobaltous ion. In other words, the complexing agent is capable of acting as a ligand in which at least one functional group can complex at a coordination site relative to the cobaltous ion. Preferably, the complexing agent has two functional groups, each functional group capable of acting as a Lewis base towards the cobaltous ion at the same time as the other functional group. Additionally, the complexing agent forms a water-soluble complex with the cobaltous ion.

Examples of suitable complexing agents include amides or a salt thereof such as urea and acetamide; amines or salts thereof such as ethylenediaminetetraacetic acid, diethanolamine and triethanolamine; sugars such as glucose, sucrose, lactose, maltose and mannitol; α-hydroxy carboxylic acids or a salt thereof such as gluconic acid, tartronic acid, saccharic acid, tartaric acid, lactic acid, malic acid and glycolic acid; α-amino carboxylic acid or a salt thereof such as aspartic acid and glutamic acid; other carboxylic acids or a salt thereof such as propanoic acid, adipic acid, malonic acid, acetic acid, citric acid and ascorbic acid.

Preferably, the complexing agent is a sugar such as glucose, lactose, maltose, and sucrose; or an α-hydroxy carboxylic acid or a salt thereof such as tartronic acid, saccharic acid, tartaric acid; or tartrate salt.

Most preferably, the complexing agent is a tartrate salt. Examples of suitable tartrate salts include those tartrate salts having a neutralizing number of counter ions selected from the group consisting of sodium, potassium, ammonium, and lithium. Combinations of these counter ions are also within the scope of the invention. For example, potassium sodium tartrate is a suitable tartrate salt. Use of lithium is best for controlling the average particle size and maintaining the hexagonal, platelet shape of the beta cobaltous hydroxide particles. Even though lithium tartrate has such an advantage, the other tartrate salts, such as sodium potassium tartrate, are more economical to use. Additionally, use of these other tartrate salts will still provide beta cobaltous hydroxide particles that can be reduced to cobalt metal particles suitable for magnetic recording applications.

According to the invention, the molar ratio of cobaltous salt to the complexing agent is about one or more. Preferably, the molar ratio of the cobaltous ion to the complexing agent is from about one to about 20. Most preferably, the molar ratio is from about two to about 10.

Particle shape and size are highly dependent upon this molar ratio. When the molar ratio is about one or more, a substantial majority of the beta cobaltous hydroxide reaction product comprises platelet-shaped, hexagonal particles. When the molar ratio is varied from about one to about 8, it has been found that the variation of the molar ratio within this range has only a minimal effect upon average particle size. When the molar ratio is greater than about 8, however, it has been found that average particle size increases as this molar ratio is increased. On the other hand, when the molar ratio is less than about one, the average particle size of the beta cobaltous hydroxide reaction product is harder to control, and substantial portions of the reaction product may not have a hexagonal, platelet shape.

Although not wishing to be bound by any particular theory, a possible rationale to explain the function of the complexing agent can be suggested. In basic solution, cobaltous hydroxide may exist as the alpha (blue) phase or the beta (pink) phase. If the alpha phase is present in solution, a blue precipitate will be seen. If the beta phase is present in solution, a pink precipitate will be seen. If both phases are present in a solution, a lavender precipitate will be seen.

In the absence of a complexing agent, the alpha phase is unstable in an aqueous, basic solution, and will dissolve and precipitate as the more stable phase, beta cobaltous hydroxide. Without a complexing agent, only minimal control over the size and shape of this precipitate is possible.

In the presence of a complexing agent such as potassium sodium tartrate, the chemistry of the aqueous, basic solution is different. The significance of this difference in chemistry substantially depends upon the molar ratio of the cobaltous ion to the complexing agent. It is an important feature of the invention that this ratio is one or more. When the ratio is one or more, the cobaltous ion is in excess. Under these conditions, only a portion of the cobaltous ion forms a water soluble complex with the complexing agent. The excess cobaltous ion in admixture surprisingly reacts to form a blue or a lavender precipitate, indicating the presence of the alpha phase. Hence, when the molar ratio of cobaltous salt to the complexing agent is about one or more, it is believed that the complexing agent not only forms a water soluble complex with the cobaltous ion, but also stabilizes the blue alpha phase in basic solution at room temperature. This is a significant feature of the invention in that the blue alpha cobaltous hydroxide apparently functions as seed particles for precipitating beta cobaltous hydroxide crystals under further hydrothermal treatment.

When the ratio of cobaltous ion to the complexing agent is less than one, there is a molar excess of the complexing agent. Under these conditions, most of the cobaltous ion is in the form of a water soluble complex. No precipitate forms, and the solution is transparent. Upon hydrothermal treatment of the transparent solution, the cobaltous complex decomposes and a precipitate forms. However, substantial portions of this precipitate may not be hexagonal or platelet-shaped particles.

The aqueous medium useful in the present invention preferably is deionized water having a conductivity of 50 $\mu$mhos or less, and more preferably 10 $\mu$mhos or less. Optionally, the aqueous medium may also comprise a surfactant. A surfactant is added to decrease the viscosity of the aqueous medium. Examples of suitable surfactants include polymethacrylate, polyacrylate, polyethylene glycol, and polyvinyl alcohol.

At least two moles of hydroxide ion are added to the aqueous solution for each mole of the cobaltous ion. This is the minimum molar ratio needed to satisfy the stoichiometric relationship between the cobaltous and the hydroxide species in the cobaltous hydroxide reaction product. When the molar ratio of the hydroxide ion to the cobaltous ion is about 2 or more, platelet-form, hexagonal beta cobaltous hydroxide particles precipitate upon hydrothermal treatment. When this molar ratio is less than about 2, the hydrothermal reaction product is not crystalline, and the cobaltous hydroxide product may not have a hexagonal, platelet shape.

Preferably, the molar ratio of the hydroxide ion to the cobaltous ion is from about 3 to about 20. when the ratio is more than 20, the presence of the excess hydroxide ion requires extensive washing after synthesis in order to lower the conductivity of the product slurry prior to drying the product.

The concentration of the hydroxide base also affects the percent carbon impurity present in the beta phase reaction product. The carbon impurity is believed to come from the complexing agent. When reacted with a cobaltous ion in aqueous solution, the complexing agent bonds to the cobaltous ion at one or more coordination sites, thereby forming a water-soluble complex. The hydroxide base tends to displace the complexing agent at the coordination sites when treated hydrothermally to form beta cobaltous hydroxide precipitate. Any non-displaced complexing agent, or carbon impurity, gets incorporated into the crystal lattice of the precipitate, resulting in a lattice defect. It is desirable to minimize such defects by minimizing the percent carbon impurity present in the beta phase reaction product. It has been found that the percent carbon impurity in the beta cobaltous hydroxide particles decreases when higher concentrations of the hydroxide base are used in the present invention.

The magnetic properties of the cobalt metal particles obtained by reduction of the beta cobaltous hydroxide particles also depend upon the concentration of the hydroxide base. It has been found that these properties improve when higher concentrations of hydroxide base are used in the present invention.

Various cations can be used as counter ions for the hydroxide base. Typically, the cation is an alkali metal cation, such as lithium, sodium, or potassium. Lithium is preferred in that use of lithium hydroxide provides excellent control over the average particle size of the beta phase reaction product. Even so, the other alkali metal hydroxides, such as sodium hydroxide, are more economical to use, and their use will still provide beta cobaltous hydroxide particles that reduce to cobalt metal particles suitable for magnetic recording applications. The hydroxide ion may also be derived from other hydroxide bases such as calcium hydroxide and magnesium hydroxide.

After all of the components have been added, the admixture is heated under hydrothermal conditions to a reaction temperature of from about 100° C. to about 268° C. The reaction temperature must be at least 100° C. to get a crystalline reaction product. Above about 268° C., the reaction product is cobaltous oxide rather than the desired beta cobaltous hydroxide.

The average size of the beta cobaltous hydroxide particles increases when synthesized at the higher reaction temperatures. It has also been found that the use of a higher reaction temperature leads to a beta cobaltous hydroxide reaction product that reduces more easily to form cobalt metal particles having higher squareness and remanent magnetization, and a narrower switching field distribution.

The composition is maintained under hydrothermal conditions at the reaction temperature for a time sufficient to precipitate the cobaltous ion as beta cobaltous hydroxide. A longer residence time in the hydrothermal reactor provides a beta phase reaction product with larger average particle size at a given temperature. Under hydrothermal conditions, the cobaltous complex decomposes in the presence of the hydroxide base, providing for the precipitation of the cobaltous ion as beta cobaltous hydroxide. It is believed that the blue alpha cobaltous hydroxide particles, which are converted into pink, platelet-shaped, hexagonal beta cobaltous hydroxide in the hydrothermal reactor, serve as seeds, or nucleation sites, for growth of the beta phase crystals.

Generally, in the method of the invention, either batch or continuous hydrothermal reaction equipment can be used with appropriate alteration of reaction time and temperature.

Analysis of powder x-ray diffraction patterns suggest that beta cobaltous hydroxide particles prepared at the higher reaction temperatures and base concentrations are more crystalline. Relative degrees of crystallinity can be determined by measuring the widths of the diffraction peaks for the beta cobaltous hydroxide particles. Crystalline material will produce sharper diffraction peaks than a material that is less crystalline. However, in the case of beta cobaltous hydroxide particles, the interpretation of the diffraction data is complicated by the fact that particle sizes less than 0.1 $\mu$m also cause the peaks to broaden. Some of the particles subjected to x-ray diffraction analysis were in the size range where both crystalline defects and particle size could yield broad diffraction peaks.

The invention will be further described by reference to the following examples.

EXAMPLE 1

Platelet-shaped, hexagonal beta cobaltous hydroxide particles were prepared in a batch hydrothermal reactor. The batch reactor was a 2 liter, stainless steel Parr reactor having a Teflon liner.

A cobaltous solution was prepared by dissolving 87 grams of cobaltous nitrate hexahydrate and 85 grams of potassium sodium tartrate in 800 ml of deionized water. The ratio of cobaltous ion to tartrate was one. A basic solution was prepared by dissolving 120 grams of NaOH in 200 ml of deionized water. The basic solution was added to the cobaltous solution. The concentration of NaOH was 3 moles per liter and the molar ratio of hydroxide ion to cobaltous ion was 10. No precipitate of pink, beta cobaltous hydroxide formed at room temperature. Instead, the resulting admixture was blue and contained colloidal particles of alpha cobaltous hydroxide.

The admixture was placed into the reactor vessel. The reactor contents were heated to about 200° C. over 70 minutes. During heating, the reactor contents were stirred at a rate of 600 rpm. The temperature was maintained at 200° C. for 30 minutes. After heating, the reactor contents were cooled to about room temperature by running tap water over the reactor. The cooled reactor contents comprised a pink slurry.

After cooling, the pink slurry was transferred to a 20 liter Pyrex washing vessel. The pink slurry in the washing vessel was washed with deionized water until the wash water had a conductivity of less than 50 μmhos. The pink slurry was passed through a filter, and pink particles were collected on the filter. The collected particles were washed twice with acetone and dried at room temperature.

Transmission electron micrographs revealed that the material was platelet-shaped, hexagonal beta cobaltous hydroxide particles having an average size of about 0.50 μm.

EXAMPLE 2

Platelet-shaped, hexagonal beta cobaltous hydroxide particles were prepared in a continuous hydrothermal reactor.

About 9000 grams of a first aqueous solution comprising about 8% by weight cobaltous in deionized water was mixed with a second aqueous solution comprising 862 grams of sodium potassium tartrate tetrahydrate in 11430 grams of deionized water. An additional 12330 grams of deionized water was added to the aqueous mixture. After adding the additional water, 4200 grams of a 50% by weight aqueous solution of NaOH was added to the mixture, thereby forming an admixture comprising the cobaltous salt, the tartrate salt, the hydroxide base, and the deionized water. In this admixture, the molar ratio of cobaltous salt to the tartrate salt was 4, the concentration of the caustic hydroxide was 1.5 moles per liter, and the molar ratio of hydroxide ion to cobaltous ion was 5.

The admixture was pumped through a continuous hydrothermal reactor. The reactor was a 160 cubic centimeter coil immersed in an oil bath maintained at 250° C. The flow rate of the admixture through the reactor was 100 cm$^3$/min. The product stream emerging from the reactor comprised a pink slurry. The slurry was washed until the conductivity of the wash water was less than about 50 μmhos. A sample of the washed slurry was collected on a filter paper and dried at room temperature. After drying, the residue on the filter paper was a pink, particulate product.

Transmission electron micrographs demonstrated that the particles were platelet-shaped, hexagonal particles having an average size of 0.1 μm. X-ray diffraction confirmed that the material was beta cobaltous hydroxide.

EXAMPLE 3

This example is intended to show that the particles of beta cobaltous hydroxide made according to the present invention can be reduced to cobalt metal particles by further processing.

A slurry emerging from the continuous hydrothermal reactor scheme of Example 2 was washed with deionized water until the conductivity of the wash water was less than 50 μmhos. The washed slurry weighed 3049 g and comprised 100 g of beta cobaltous hydroxide. Next, an anti-sintering agent was adsorbed onto the beta cobaltous hydroxide. To accomplish this, the washed slurry was homomixed with 62.5 ml of a NaOH solution prepared by dissolving 18 grams NaOH in 250 ml of deionized water and 62.5 ml of a solution prepared by dissolving 56 grams Al(NO$_3$)$_3$.9H$_2$O in 250 ml of deionized water. The slurry was washed with deionized water until the conductivity of the wash water was less than about 50 μmhos. The washed particles were collected on filter paper and air dried at room temperature. The dried particles were crushed to pass through a No. 10 mesh screen.

About 50 grams of the crushed particles of beta cobaltous hydroxide were then reduced to cobalt metal particles. To accomplish this, the crushed particles were placed into a 2 inch by 16 inch fluidized bed made from quartz and pre-heated to 450° C. in a nitrogen purge entering the base of the fluidized bed. The flow rate of the nitrogen purge was 30 cubic feet per hour. The contents of the fluidized bed were maintained at a temperature of about 450° C. for 30 minutes. As a result of the pre-heating, the beta cobaltous hydroxide was dehydrated to cobaltous oxide. The purpose of the pre-heating was to minimize crystallographic defects in the particles prior to reduction. After pre-heating, the temperature was lowered to 400° C. and the purge gas was changed from nitrogen to hydrogen for conversion to cobalt metal. The flow rate of the hydrogen purge was 80 cubic feet per hour. These reducing conditions were maintained for 30 minutes. After this time, the contents of the fluidized bed were cooled to room temperature under a nitrogen purge of 50 cubic feet per hour. After cooling, the reduction product was transferred to a nitrogen-purged glove box for further analysis.

X-ray diffraction confirmed that the reduction product was predominantly cobalt metal particles. The magnetic moment of the cobalt metal product was 131 emu/g with a squareness of 0.69. The coercivity was 840 Oe. The switching field distribution was 0.91 and the magnetic remanence, Br, was 2020 Gauss.

EXAMPLE 4

Electromagnetic performance of cobalt metal particles prepared by the method of Example 3 was evaluated by grinding the cobalt metal particles with 7% by weight of tridecyl polyethyleneoxide phosphate ester surfactant such that the solids were 80% by weight in toluene. More specifically, 16.0 grams of the cobalt metal, 1.1 grams of tridecyl polyethyleneoxide phosphate ester surfactant and 4.3 grams of toluene were mixed and ground with 200 grams of a stainless steel media in a mill for 60 minutes. After grinding, a polymeric binder and a sufficient amount of methyl ethyl ketone were added such that the solids were 50% by weight. To accomplish this, 10.5 grams of the binder and 10.3 grams of methyl ethyl ketone were added to the mill. The binder was prepared by mixing 570 grams of vinyl chloride vinyl acetate resin (VYHH vinyl resin from Union Carbide Corporation), 187.5 grams of dioctyl phthalate, and 1222 grams of methyl ethyl ketone. After adding the binder and the methyl ethyl ketone, the mixture was milled for about an additional 15 minutes to form a cobalt metal dispersion for electromagnetic testing.

EXAMPLE 5

Samples of beta cobaltous hydroxide were prepared in a continuous hydrothermal reactor in order to determine the size of the beta cobaltous hydroxide particles as a function of temperature. For samples 1-5, the flow rate of reactants through the reactor was 100 cm$^3$/min. The concentration of NaOH was 2M. The cobaltous ion to tartrate molar ratio was held constant at 2. For samples 6-10, the flow rate was decreased to 50 cm$^3$/min. For each sample, size was measured in terms of the nitrogen specific surface area of the particles. A larger nitrogen specific surface area corresponds to a smaller particle. The results are shown in Table 1:

TABLE 1

| Sample | Temperature (°C.) | Nitrogen Specific Surface Area (m$^2$/g) |
| --- | --- | --- |
| 1 | 175 | 96 |
| 2 | 200 | 75 |
| 3 | 225 | 52 |
| 4 | 250 | 26 |
| 5 | 275 | 13 |
| 6 | 175 | 85 |
| 7 | 200 | 63 |
| 8 | 225 | 39 |
| 9 | 250 | 18 |
| 10 | 275 | 13 |

These results show that particle size increases at higher temperatures. These results also show that increasing the residence time by decreasing the flow rate from 100 cm$^3$/min to 50 cm$^3$/min slightly increased the average particle size at a given temperature.

Electron micrographs revealed that the particles were hexagonal from 175° C. to 250° C., but were not hexagonal at 275° C. Powder x-ray diffractions confirmed that the particles produced at 250° C. and below were beta cobaltous hydroxide, while the particles produced at 275° C. were cobaltous oxide.

Other embodiments of this invention will be apparent to those skilled in the art from a consideration of this specification or practice of the invention disclosed herein. Various omissions, modifications, and changes to the principles described herein may be made by one skilled in the art without departing from the true scope and spirit of the invention which is indicated by the following claims.

What is claimed is:

1. A composition that is an admixture of ingredients comprising blue cobaltous hydroxide and a complex of cobaltous ion and a complexing agent, said composition being formed by combining the following materials:
   a) the cobaltous ion;
   b) the complexing agent wherein the complexing agent is selected from the group consisting of an α-hydroxy carboxylic acid; a salt of an α-hydroxy carboxylic acid; an α-amino carboxylic acid; a salt of an α-amino carboxylic acid; and mixtures thereof, and
   wherein the cobaltous ion is in excess relative to the complexing agent;
   c) a sufficient amount of hydroxide ion such that the molar ratio of the hydroxide ion to the cobaltous ion is more than about 2; and
   d) an aqueous medium.

2. The composition of claim 1, wherein the complexing agent is a tartrate salt.

3. The composition of claim 2, wherein the tartrate salt is selected from the group consisting of sodium tartrate, potassium tartrate, lithium tartrate, and potassium sodium tartrate.

* * * * *